(12) United States Patent
Waldinger et al.

(10) Patent No.: US 6,685,643 B1
(45) Date of Patent: Feb. 3, 2004

(54) METHOD AND DEVICE FOR RECORDING ULTRASONIC IMAGES

(75) Inventors: Johannes Waldinger, Neubiberg (DE); Dietmar Kaiser, Moosburg (DE); Bernhard Mumm, Mammendorf (DE); Kiyoji Miyamoto, Tokyo (JP)

(73) Assignee: Tomtec Imaging Systems GmbH, Unterschleibheim (DE)

( * ) Notice: Subject to any disclaimer, the term of this patent is extended or adjusted under 35 U.S.C. 154(b) by 0 days.

(21) Appl. No.: 09/763,276

(22) PCT Filed: Aug. 12, 1999

(86) PCT No.: PCT/EP99/05854

§ 371 (c)(1), (2), (4) Date: May 22, 2001

(87) PCT Pub. No.: WO00/11495

PCT Pub. Date: Mar. 2, 2000

(30) Foreign Application Priority Data

Aug. 21, 1998 (DE) .......................... 198 38 140

(51) Int. Cl.[7] .................................. A61B 8/14
(52) U.S. Cl. .................. 600/444; 600/445; 600/437
(58) Field of Search ........................... 600/444, 445, 600/447, 437, 441, 450, 453, 454, 456, 457, 466

(56) References Cited

U.S. PATENT DOCUMENTS

| | | | |
|---|---|---|---|
| 4,756,313 A | * 7/1988 | Terwilliger | 600/462 |
| 5,105,819 A | * 4/1992 | Wollschlager et al. | 128/916 |
| 5,159,931 A | * 11/1992 | Pini | 600/141 |
| 5,506,605 A | * 4/1996 | Paley | 345/163 |
| 5,529,070 A | * 6/1996 | Augustine et al. | 600/443 |
| 5,540,229 A | * 7/1996 | Collet-Billon et al. | 600/443 |
| 5,562,095 A | * 10/1996 | Downey et al. | 128/916 |
| 5,575,286 A | * 11/1996 | Weng et al. | 600/425 |
| 5,609,485 A | * 3/1997 | Bergman et al. | 434/262 |
| 5,655,535 A | * 8/1997 | Friemel et al. | 128/916 |
| 5,924,989 A | * 7/1999 | Polz | 600/443 |
| 5,924,991 A | * 7/1999 | Hossack et al. | 600/443 |

* cited by examiner

Primary Examiner—Marvin M. Lateef
Assistant Examiner—William Jung
(74) Attorney, Agent, or Firm—Sheridan Ross P.C.

(57) ABSTRACT

The invention relates to a method or a device for recording ultrasonic images of an object (1) in which ultrasonic waves are radiated onto the object (1) by an ultrasonic emitter, and ultrasonic waves reflected by the object (1) are received by an ultrasonic receiver. For recording individual image partial areas (6), the ultrasonic emitter or ultrasonic receiver (18) is displaced along the object (1) or is at least partially rotated with regard to the object (1). The corresponding movement (S) of the ultrasonic transmitter or of the ultrasonic receiver (4, 18) is progressively detected by a detector (9, 23) and is assigned to the individual image partial areas (6). As a result, it is possible to record the object (1) by manually moving the ultrasonic transducer (4), whereby an incremental detector serves as a detector (9, 23) for progressively detecting the movement (S). The distances ($\delta$, $\delta\alpha$) between individual image partial areas (6) can be then be determined by evaluating the progressively detected positions of the ultrasound transducer (4) which are then assigned to the individual image partial areas (6).

28 Claims, 4 Drawing Sheets

METHOD AND DEVICE FOR RECORDING ULTRASONIC IMAGES

The present invention relates to a method and a device for recording ultrasonic images, specifically for real-time recording and displaying three-dimensional ultrasonic images, in accordance with the introductory clauses of claims 1 and 12, as well as to the application of this method or this device in accordance with the claims 17 to 19.

Such methods and devices for recording ultrasonic images of an object are known, wherein an ultrasonic emitter emits ultrasonic waves onto an object while an ultrasonic receiver receives the ultrasonic waves reflected by the object. For recording the object, the ultrasonic emitter or the ultrasonic receiver, respectively, is displaced along the object or rotated relative to the object while individual image sub-areas of the object are recorded. As a rule, these partial image areas correspond to a linewise scanning of the object, in which operation the object is recorded by lines along a recording direction in which the ultrasonic emitter or the ultrasonic receiver is displaced. In the known ultrasonic devices, the images generated in the ultrasonic device can be transferred in digital form or via a video output into a post-processing device or into a data processing system, respectively. There the images can be stored or directly post-processed.

With the scanning operation the object to be examined is recorded by lines, which means that individual "layers" of the object, which are parallel to each other, or "slices" of the object, which are in mutual rotational symmetry, are exposed to ultrasonic waves and that the corresponding reflected ultrasonic waves are received in the ultrasonic device. The received ultrasonic waves are processed in the data processing system such that a halftone image is produced on a display device, with the individual halftones corresponding each to ultrasonic waves reflected more strongly or weakly.

The individual layers or slices of the object, i.e. the individual lines recorded in the ultrasonic scanning operation are "superimposed" in the data processing system so as to obtain a three-dimensional representation of the object on the display device. The different spacings of various regions of a layer, i.e. the position of cavities or regions of more strongly compacted material of the object relative to the ultrasonic device, are obtained by evaluation of the halftone information of each layer.

A sound transmitting medium, which enhances the propagation of ultrasonic waves, is provided between the ultrasonic device and the object to be recorded. This sound transmitting medium is represented by a uniform halftone in the corresponding halftone image. In particular, the outside contours of an object can be determined by the provision that the first halftone variations on the boundary between the sound transmitting medium and the object to be examined are detected in the halftone image and that their respective relative spacing from the ultrasonic device is measured.

The ultrasonic methods make use of a pre-defined halftone grade (threshold) or a grade to be computed in order to find contours in the image. The contour information is then stored in an image and, after evaluation of the respective spacings between the ultrasonic device or the ultrasonic transmitter, respectively, and the outside contours of the object to be examined, furnish then a three-dimensional impression of the image.

These known ultrasonic methods are suitable, for instance, for examining a foetus inside the mother's abdominal cavity or for detection of renal calculi inside the human body. For recording the object to be examined, which is located, for instance, inside the human body, the ultrasonic device is connected to the skin surface on the human body by means of a sound transmitting medium such as a gel, oil or waters and is then moved or rotated along a desired recording direction whilst ultrasound images are recorded during uniform distances in time or space. The entire scanning operation extends over a defined area of the human body, with individual layers or slices of the object under examination inside the body being recorded during the scanning operation in succession. The individual ultrasonic images are then joined in a spatially correct succession in a subsequently employed data processing system so that a complete or three-dimensional image of the object is achieved by "superimposition" of the individual images. Then "artificial" two-dimensional images in this three-dimensional image can be calculated in the data processing system.

Ultrasonic techniques employed in practical clinical applications for the three-dimensional recording of human organs are presently operating on a tomography basis, which means that the volume is composed of the individual recorded layer planes or slices. In trans-oesophageal echo cardiography, for example, a pivotable endoscopic probe is introduced through the patient's oesophagus. The ultrasonic sensor is integrated as so-called "phased array" into the tip of the probe. In this technique the ultrasonic transducer on the tip of the probe is linearly shifted or rotated so that a layer of the organ is scanned from each angular position of the rotating ultrasonic transducer or from each shifted probe position. One image sequence, i.e. one or several cycles of movement of the organ, such as a cardiac cycle, is produced per layer.

When such a sequence has been recorded the rotation of the ultrasonic transducer is continued by a desired angular increment, using a motor such as a stepping or linear motor, or the transducer is shifted by hand or along a linear path in the case of linear shift. Then a data processing system triggers the next recording sequence, with this data processing system being capable of processing both the data of the electro cardiogram (ECG) and the respiratory or thorax movements (respiration scan).

With coupling the ECG to the recording times an attempt is made to record each image of a sequence always at a defined phase point during the cycle of the hear beat. As a result, it is possible to generate sequences of three-dimensional images of moved objects or organs inside organisms, which, when joined in succession, furnish a three-dimensional representation of the organ as a function of time. The organ movement can then be cyclically viewed as in a "film".

It is particularly important in these methods that the distances between the individual "layers", i.e. between the individual image sub-areas of the object under examination, are almost constant in order to avoid a longitudinal distortion of the overall image along the recording direction, i.e. along the scanning axis. In order to achieve a uniform recording rate, i.e. a uniform rate of the ultrasonic transducer along the recording direction during the scanning operation, the conventional techniques either operate on motor-controlled mechanical systems for moving the ultrasonic device or magnetic position detectors or optical systems for detecting the respective precise position of the ultrasonic device with respect to the corresponding record of the image sub-area, i.e. the corresponding "layer" of the object under examination. Due to the detection of the precise position of the ultrasonic device during the operation of recording such a "layer" it is possible later on to compose the individual image sub-areas, i.e. the individual "layers" of the object examined, in the data processing system in a form corresponding to reality. In the conventional systems image distortions along the recording direction can hence be avoided.

From the German Patent DE 38 29 603 A1, for example, an ultrasonic endoscopic device is known that is provided, over a distal terminal section, with a flexible hose accommodating a longitudinally displaceable ultrasonic transducer on a slide for the creation of multi-plane tomograms. In this case, too, a defined volume is to be scanned in multiple planes with high precision in order to be able to reconstruct a precise three-dimensional representation of the sectional images so obtained. There the slide is displaced by an associated Bowden cable operated by a motor along the distal terminal section for appropriately recording the individual layer images.

The U.S. Pat. No. 5,159,931 discloses a rotating ultrasonic probe which records individual slices in rotational symmetry of the organ under examination; there the probe is equally rotated by means of a motor that rotates the probe by increments in correspondence with a specified succession of increments so that the precise position is known for each recorded layer plane or each slice, respectively, so as to permit an assignment of the individual image sub-areas of the rotational images with each other in the data processing system.

These conventional systems present the disadvantages that the respective ultrasonic equipment is highly complex and very expensive to manufacture, that the recording method is very complicated to handle, and that the operator, i.e. the physician examining a heart, must expect very long recording and post-processing times.

The known motor-controlled recording systems equipped with motors, which record the respective organs both in parallel and by means of a so-called "sweep" or by a rotation of the ultrasonic transducer, moreover require a permanent calibration of the respective motors, a motor controller, as well as the supply of energy up to the region of the organs in organisms inside which the motors are moved, which involves potential risks for the patient. Even the known systems provided with position sensors (cf., for instance, the German Patent DE 196 08 971 A1) require a complex expenditure in terms of apparatus as well as the calibration of the systems and possibly a so-called "reset" position in order to be able to determine the initial position of the ultrasonic transducer by the beginning of the ultrasonic recording cycle.

The present invention is now based on the problem of improving the methods and devices of the aforementioned general type in an approach to render motor-controlled mechanical systems or position detections of the ultrasonic transducer dispensable whilst a simple, low-cost ultrasonic method or ultrasonic device is proposed that is easy to handle.

The present invention solves the afore-defined problem by the features defined in the characterising clauses of claims 1 and 12. Expedient embodiments of the invention are characterised in the respective dependent claims; some applications of the inventive device or of the respective method are identified in the claims 16 and 17. In accordance with the present invention an object to be examined, that is located, for instance, in an inaccessible body or part of the body, is recorded by means of an ultrasonic device. There, the ultrasonic transducer, that contains expediently the ultrasonic emitter and the ultrasonic receiver, is moved, rotated or pivoted in a fan pattern along the recording direction whilst individual image sub-areas of the object, i.e. individual "layers" or slices of the object are recorded. These layers are stored in a data processing system and evaluated on the basis of the aforementioned halftone analysis. Then the layers are composed again with reference to the recorded succession so that a three-dimensional ultrasonic image of the object under examination will be obtained.

The resulting image may be displaced in two-dimensional or three-dimensional form; possibly a plurality of these two- or three-dimensional images may be joined in succession to produce moving images, so-called four-dimensional images. These images can also be marked in colours so as to achieve an impression of the object under examination that is easier for the operator to survey. In addition to this halftone information (B mode) it is also possible to detect the colour, movement or flow information ("colour flow") or any other additional video information in the same manner. With this technique several images are taken of one site of the moving object, with the respective images (a plurality of image sub-areas) of a condition of movement of the object being composed to form a respective resulting image. The plurality of resulting images in succession then furnishes a moving representation of the object (film projection).

To determine the precise succession of the individual layers or slices of the individual image sub-areas and for establishing, in particular, the respective distances between the individual layer planes, the movement of the ultrasonic emitter or the ultrasonic receiver, respectively, is detected in increments by means of a detector and then associated with the individual image sub-areas. The ultrasonic transducer when moved by hand, for instance by the physician, can be displaced or rotated along the object while an increment detector serves to sense the incremental detection of the movement.

The ultrasonic emitter or the ultrasonic receiver, respectively, is expediently displaced or rotated along the recording direction at a uniform speed so as to obtain sectional planes spaced from each other by approximately the same distance, even though this would actually not be necessary on account of the increment detector. The mutual spacings of the individual image sub-areas are determined by the analysis of the positions of the ultrasonic sensor or the ultrasonic receiver, respectively, which are detected by steps and which had previously been associated with the individual image sub-areas. When objects are recorded it is expedient, for instance, to displace or rotate the ultrasonic transducer at a uniform speed while the corresponding image sub-areas are either passed on via image data lines to a data processing system or buffered in the ultrasonic equipment. At the same time, the increment detector or the. detector, respectively, communicates the lengths of the individual steps in the movement or rotation of the ultrasonic transducer, which are then associated with the individual image sub-areas in correspondence with the time lapsed. In this operation it is also possible to attach the corresponding positions of the ultrasonic transducer, which are determined via the increment detector, together as so-called "headers" to that data package that corresponds to an isolated image sub-area.

In particular, the number of the incrementally detected positions is approximately the same or even higher than the number of the recorded image sub-areas so that it will be ensured that at least one position of the ultrasonic transducer will be available for each image sub-area. With the recording of the individual image sub-areas and the detection of the positions by the increment detector mostly not being synchronised in this very plain system, the detection of a plurality of different positions is recommended so that the correspondingly precise position can be detected for each image sub-area and associated with the latter with a very high degree of approximation.

For recording moving objects such as a heart the states of motion or the absolute or relative time stamps (i.e. relative to an event such as the occurrence of the ECG R-peak) of a moving object are detected in addition to the images of the individual image sub-areas, whereupon the incrementally detected positions and the individual image sub-areas are associated with the states of motion of the object.

Subsequently, the incrementally detected positions and time stamps are associated with the images of the individual image sub-areas in the aforedescribed manner and then composed and displayed in correspondence with the states of motion of the object. With this technique the aforementioned "four-dimensional" images are achieved. Here the points of time for recording individual image sub-areas of the moving object are expediently controlled by the movements of the object as such. To this end signals of the electrocardiogram, the respiration, the movements of the stomach, the peristalsis of the oesophagus or a combination of these signals from the organism are employed for determining the points of time by which the individual image sub-areas are recorded. The ultrasonic emitter or the ultrasonic receiver, respectively, may be moved along linear, circular, bow-shaped or free-hand lines along the object, with appropriate increment detectors or detectors being applied in correspondence with the movement for incremental detection of the movement of the ultrasonic transducer. The individual regions of the object, which present different intensities in correspondence with the recorded halftone images and/or colour information, or differently moving areas of the object can be identified by colour markings in the display in order to facilitate the detection of the individual regions of the organ for the physician.

In this manner it is possible to process and/or display the images formed from the individual image sub-areas in real time while the object is recorded so that the physician can examine the organ manually for better observation of the progress during an operation, for example.

Mechanical, optical or electromagnetic motion sensors known from prior art already may be used as increment detectors for incremental detection of the movement. Examples are the systems known from a "computer mouse" for detecting the mouse movements by means of optical sensors or spherical detectors determining the sensor movement in two dimensions. Moreover, rotationally symmetrical increment detectors are suitable to detect the linear movement of an ultrasonic transducer. When the ultrasonic transducer is freely moved in space correspondingly designed mechanical systems are suitable for the incremental detection of all degrees of freedom of the ultrasonic transducer. It is also particularly advantageous to integrate the increment detector into the ultrasonic transducer and to provide appropriate measuring detectors or transducers for the incremental detection of the movement of the ultrasonic transducer relative to its surroundings. This is possible, for instance, with spherical bodies on the outside shell of the ultrasonic transducer, which detect this relative movement by increments as the ultrasonic transducer is moved along a surface.

The inventive method or the inventive device, respectively, is particularly suitable for recording the heart of an organism in consideration of the movement of the heart for displaying a moving, specifically four-dimensional image. With this technique it is possible to record the organ of the organism or parts of this organ by means of an ultrasonic method with trans-thoracic, trans-oesophageal, abdominal, trans-rectal or trans-vaginal application, and moreover by intra-vascular or intra-ductal application when an ultrasonic catheter technique is employed. Furthermore free-hand recording with an ultrasonic transducer moved by the physician on the patient's body surface or, with an intra-operative technique directly on or in the organ can be realised in a manner similar to the control of a computer "mouse".

In the following, some preferred embodiments of the invention will be explained in more details with reference to the attached drawings wherein.

Figure 1:
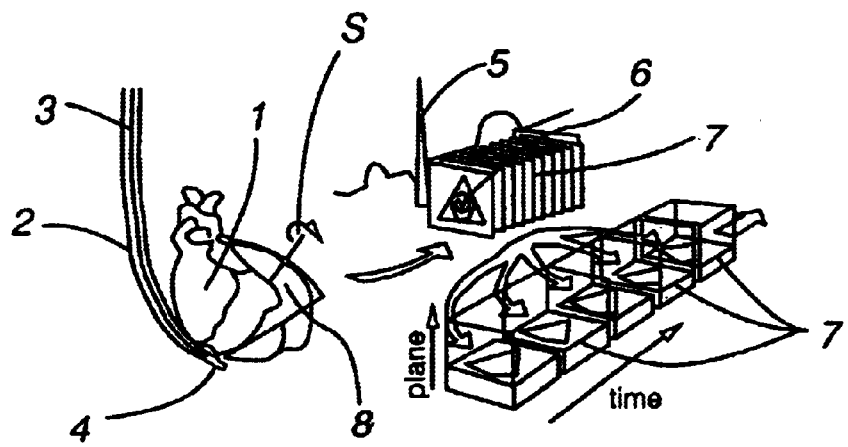
FIG. 1 is a schematic of the operation of recording a heart.

FIG. 1 is a schematic view illustrating the operation of recording an object 1, such as a heart, that is recorded through the oesophagus. To this end an ultrasonic transducer 4 is introduced through the oesophagus 2 by means of a flexible tubing 3 for recording parallel or rotationally symmetrical images 7 of the object 1. In this operation a tomographic ultrasonic plane or section 8, for instance, that is formed by ultrasonic beams, is rotated in the direction of rotation S in a rotationally symmetrical form.

The individual image sub-areas 6 spaced from each other by the distance δx are triggered by means of an ECG signal and correspondingly associated with each other. The individual image sub-areas 6 in a superimposed arrangement produce one image 7 reflecting a certain state of motion of the object 1. The individual images 7 may then be displayed in succession on the screen of a data processing system with the production of a four-dimensional—i.e. moving three-dimensional—representation of the object 1.

Figure 2:
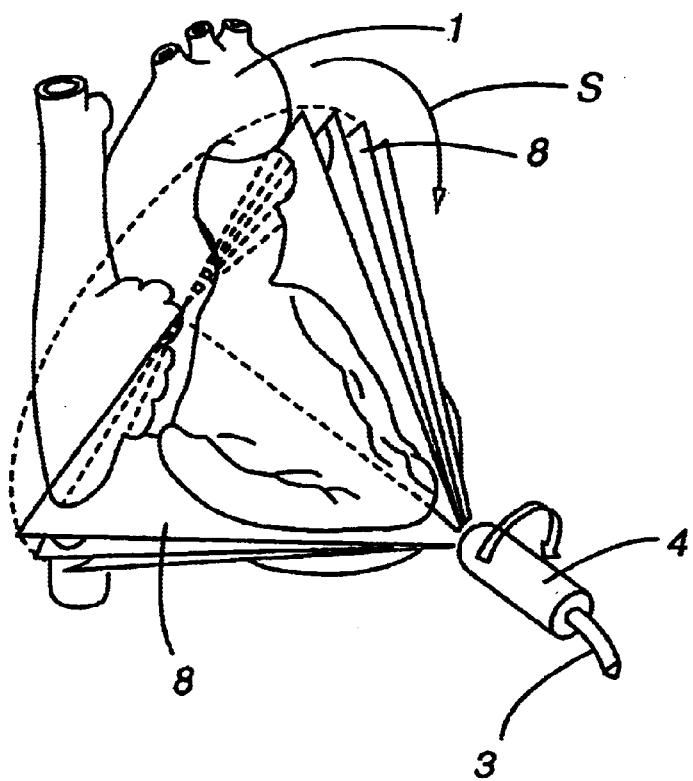
FIG. 2 shows a rotationally symmetrical ultrasonic transducer for recording a heart.

FIG. 2 illustrates a rotationally symmetrical ultrasonic transducer 4 connected to the flexible tubing 3. The ultrasonic transducer emits rotationally symmetrical tomographic ultrasonic planes or sections 8 constituted by ultrasonic beams, which sections rotate in a direction of rotation S for recording the object 1. The individual layer planes of the rotationally symmetrical images are spaced by the distance δα.

Figure 3:
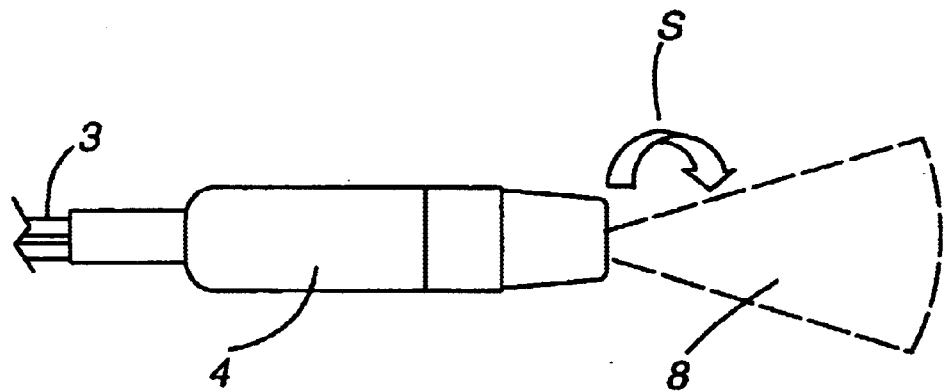
FIG. 3 is a view of an ultrasonic transducer for trans-thoracic echo cardiography.

FIG. 3 illustrates the ultrasonic transducer 4 according to FIG. 2 with the connected flexible tubing 3 that may be configured also as a cable, for instance, as well as the tomographic ultrasonic planes or sections 8 formed by ultrasonic beams ands the direction of rotation S.

Figure 4:
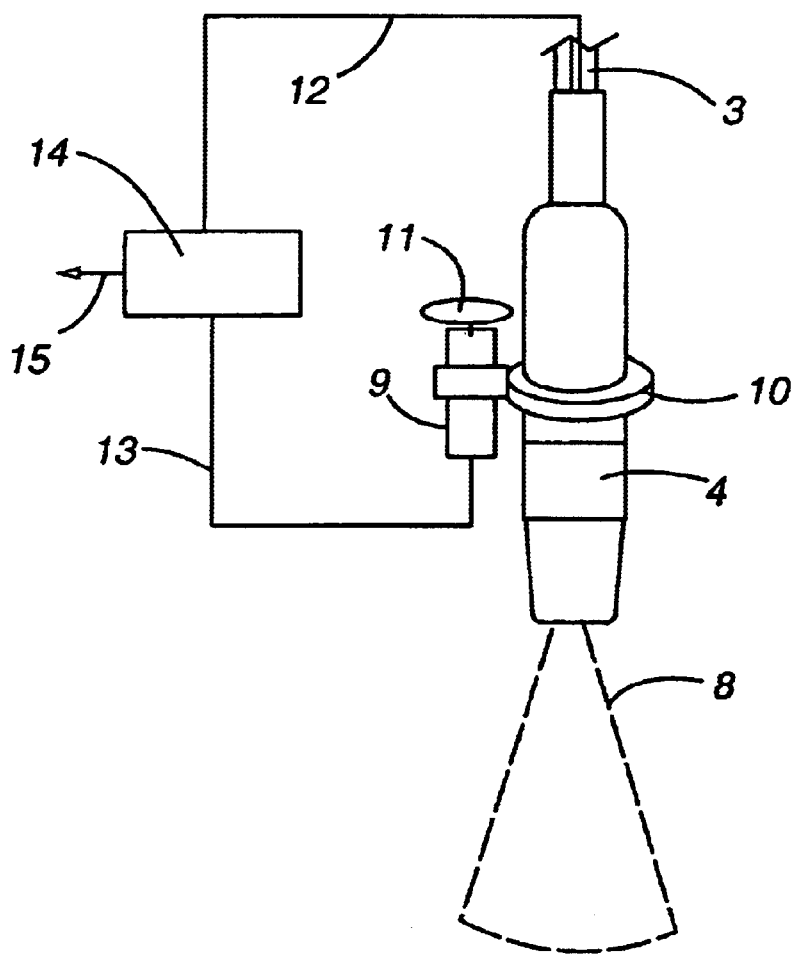
FIG. 4 shows the ultrasonic transducer according to FIG. 4 with the increment detector connected thereto.

FIG. 4 is a schematic of the ultrasonic transducer 4 according to FIG. 3 with the flexible tubing 3 that is adapted to accommodate both image data lines 12 and, if necessary, also position data lines 13. An increment detector 9 is connected to the ultrasonic transducer 4 emitting rotationally symmetrical tomographic ultrasonic planes or section 8 formed by ultrasonic beams, by means of a mount 10; this increment detector detects the rotational movement of the ultrasonic transducer 4 in steps by means of an increment transmitter 11 such as a small wheel. With this configuration the ultrasonic transducer 4 is rotated either by hand or by means of a Bowden cable that may equally be provided through the flexible tubing 3. The image data lines 12 and the position data lines 13 end in a data processing system 14 that associates the individual image sub-areas 6 with each other by means of the increment tally detected positions of the detector 9 and passes them on via an image data line 15 for display to a further data processing system.

Figure 5:
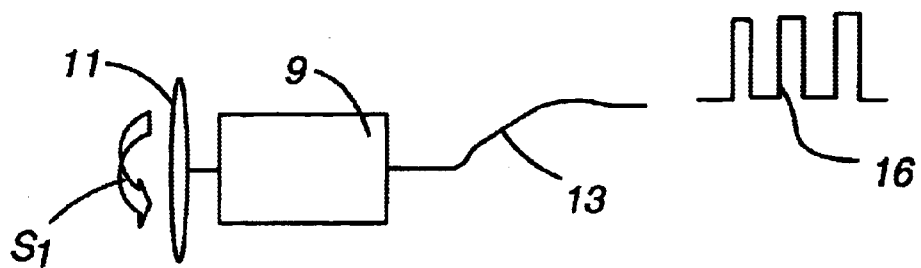
FIG. 5 is a view of the increment detector with the output signal.

FIG. 5 is a view of the detector 9, i.e. the increment detector with the position data line 13 and the increment transmitter 11 connected thereto, which detector records the movement of the ultrasonic transducer 4 or the ultrasonic transmitter or receiver 18, respectively, in steps along the incremental direction $S_r$. The position data line 13 supplies the corresponding pulses 16 to the data processing system 14 that associates the individual positions or pulses 16 of the detector 9 with the image sub-areas 6 with reference to the points of time of the recorded image sub-areas 6. It is also possible to supply the direction of movement S via a second detector signal to the data processing system 14, in addition to the movement pulses. 16.

Figure 6:
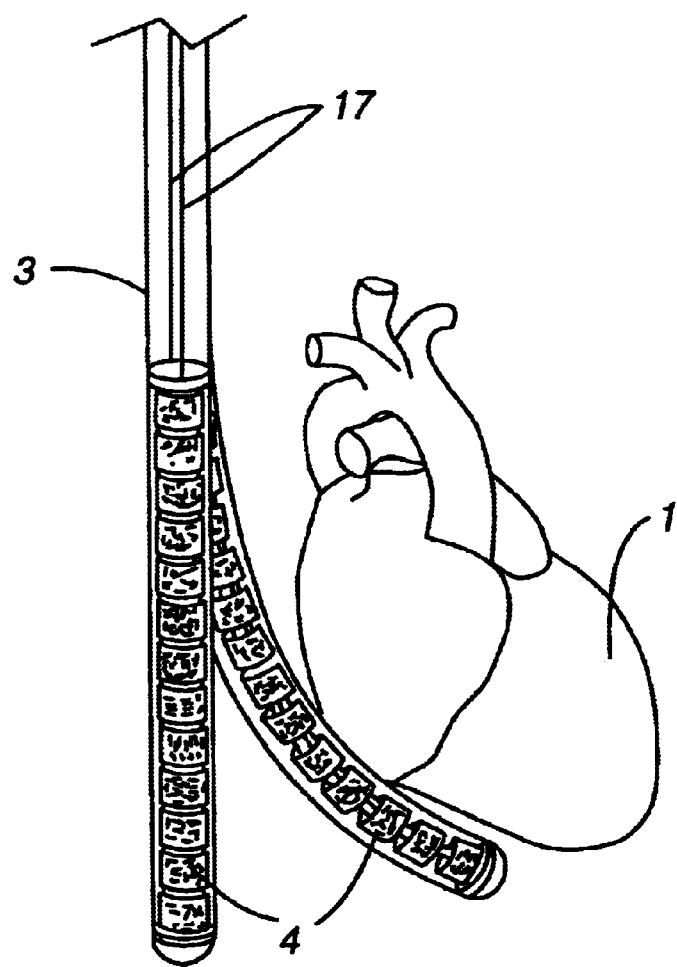
FIG. 6 shows a linear ultrasonic transducer for recording the heart in parallel.

FIG. 6 illustrates another embodiment of a linear ultrasonic transducer 4 that is guided inside the flexible tubing 3 to the periphery or the vicinity of the object 1 such as a heart. Pull cords 17 arranged inside the flexible tubing 3 for mechanical control of the ultrasonic transducer 4 are used for guiding, i.e. introducing and extracting, the ultrasonic transducer 4. In the aforedescribed examples it is also possible to replace the pull cords 17 by a Bowden cable or other devices such as a mechanical shaft that is disposed inside the flexible tubing 3 for enabling the rotation or sliding movement of the ultrasonic transducer 4. In FIG. 6, however, a linear ultrasonic transducer 4 is illustrated, i.e. a longitudinally displaceable ultrasonic transducer 4 that is moved slowly from the bottom upwards or vice versa by means of the pull cords 17.

Figure 7:
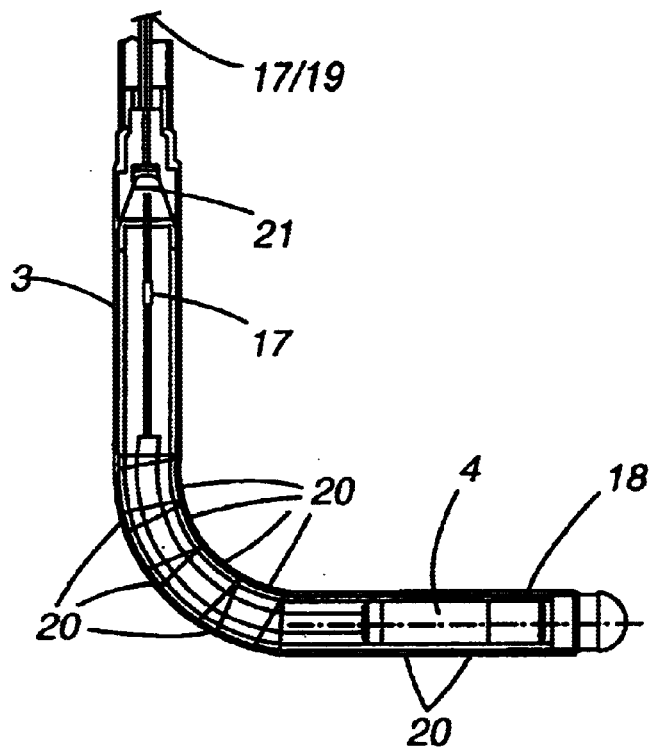
FIG. 7 is a sectional view of the linear ultrasonic transducer according to FIG. 6 with position detectors.

FIG. 7 is a sectional view taken through the linear ultrasonic transducer 4 according to FIG. 6 with the corresponding ultrasonic emitter or receiver 18 at the top of the ultrasonic transducer 4 inside the flexible tubing 3. Motion sensors 20, which may be both optical or mechanical or electromagnetic devices, detect a linear movement of the ultrasonic transducer 4 by means of the pull cords 17 passed upwards through the flexible tubing 3. The position signals, i.e. the incremental detection of the linear movement of the ultrasonic transducer 4 by means of the motion sensors 20, are supplied into a signal line 19 in a signal coupler 21. This signal line 19 may be a fibre-optical light guide that passes the optical position signals from the motion sensors 20 to the data processing system 14, or also a power line carrying electro-magnetically detected movements of the ultrasonic transducer 4. The signal line 19 may consist of a mechanical wire that passes mechanical displacements of the motion sensor 20 through the flexible tubing 3 to the outside by means of the signal coupler 21.

Figure 8:
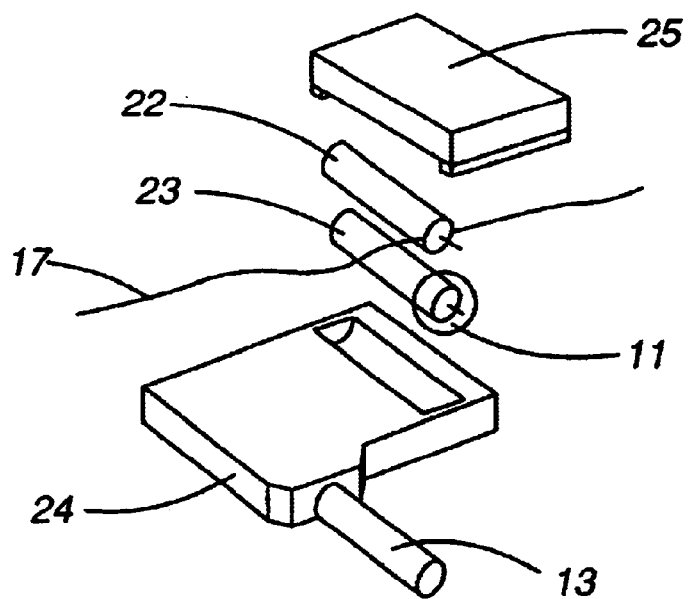
FIG. 8 shows an increment detector for detecting the linear movements of the ultrasonic transducer.

FIG. 8 is an illustration of another embodiment of a detector 9 in the form of a detector roller 23 that is pressed against a press roller 22 for detecting the relative movements of the pull cords 17 drawn through the gap between the detector roller 23 and the press roller 22. Both the detector roller 23 and the press roller 22 are located inside a bottom housing 24 and a top housing 25 for detecting the rotational movements of the detector roller 23 by means of the increment transmitter 11 and for passing the incremental position of the corresponding pull cord 17 so detected via a position data line 13 on to the data processing system 14. It is also possible to use the ultrasonic catheter as such, instead of the pull cord 17, which is employed in trans-ductal or intra-vascular ultrasonic recording operations.

With the inventive method the calibration and the provision of a motor (such as a stepping motor) become superfluous. Moreover, the motor controller for controlling the stepping motor and the supply of energy for motor control are omitted. What is not necessary either are position sensors for detecting an ultrasonic transducer that is displaced along the organism body outside the body of the organism for recording organs. The appropriate inventive increment detectors are inexpensive and are suitable to detect the respective position of the ultrasonic transducer 4 or the ultrasonic emitter or receiver 18, respectively, in steps with a high precision. The methods so far known for triggering the appropriately recorded image sub-areas 6 in dependence on the respiratory situation or the phase of the cardiac cycle can moreover be equally performed with this inventive method or the inventive device, respectively.

What is claimed is:

1. Method of recording ultrasonic images of an object comprising:

emitting ultrasonic waves onto the object by means of an ultrasonic emitter, and by receiving ultrasonic waves reflected by the object by means of an ultrasonic receiver, wherein said ultrasonic emitter and/or said ultrasonic receiver is/are displaced and/or rotated, at least partly, relative to said object for recording individual image sub-areas and wherein said object is recorded by a manual movement of said ultrasonic emitter and/or said ultrasonic receiver, the positions of said ultrasonic emitter and/or said ultrasonic receiver, relative to said object, are incrementally detected by means of a separate detector and associated with the individual images sub-areas, and said detector is mounted on said ultrasonic emitter and/or said ultrasonic receiver and measures the position of the ultrasonic emitter and/or receiver mechanically or optically.

2. Method according to claim 1, wherein an increment transmitter serves as detector for incremental detection of the movement, and the positions of said ultrasonic emitter and/or said ultrasonic receiver, relative to said object, are detected in a manner not synchronized with the recording of individual image sub-areas of said object.

3. Method according to claim 1, wherein said ultrasonic emitter and/or said ultrasonic receiver is displaced or rotated along the recording direction at a uniform speed.

4. Method according to claim 1, wherein the distances by which individual image sub-areas are spaced from each other are determined by the analysis of the incrementally detected positions of said ultrasonic emitter and/or said ultrasonic receiver, which positions had been associated with the individual image sub-areas.

5. Method according to claim 1, wherein the number of said incrementally detected positions is approximately equal to or higher than the number of the recorded image sub-areas.

6. Method according to claim 1, wherein
the states of motion of a moving object are detected in addition to the recorded images of the individual image sub-areas, the incrementally detected positions and the individual image sub-areas are associated with the states of motion of said object, and said incrementally detected positions are associated with the recorded images of the individual image sub-areas and the latter are composed and displayed in correspondence with the states of motion of said object.

7. Method according to claim 6, wherein
the points of time by which individual image sub-areas of said object are recorded are controlled by the movements of said object.

8. Method according to claim 6 for recording a human or animal organ, wherein
the points of time by which individual image sub-areas are recorded are controlled by signals of the electrocardiogram, the respiration, the movement of the stomach, the peristalsis of the oesophagus or by a combination of these signals from the organism.

9. Method according to claim 1, wherein
said ultrasonic emitter and/or said ultrasonic receiver is moved along said object along linear, circular, bow-shaped or free-hand lines.

10. Method according to claim 1, wherein
in addition to halftone information of individual regions of said object color, motion or flow information or any other additional video information is detected in the representation of differently moving regions of said object in particular.

11. Method according to claim 1, wherein
said images formed by the image sub-areas are processed and/or displayed in real time while said object is recorded.

12. Method according to claim 1 for the three-dimensional recording of an organ, particularly the heart in an organism, in consideration of the movement of the heart for the display of a moving image.

13. Method according to claim 1 for trans-thoracic (TTE), intra-vascular(IVUS), trans-oesophageal (TEE) or intra-ductal (IDUS) as well as abdominal, trans-rectal, trans-vaginal, trans-cranial and/or intra-operative ultrasonic recording.

14. Method according to claim 1 for-intra-vascular (IVUS) or iritra-ductal (IDUS) ultrasonic recording with application of a catheter.

15. Method according to claim 1, wherein
said increment detector is detecting the rotational movement of the ultrasonic transducer in steps by means of a wheel.

16. Method according to claim 1, wherein
said increment detector is a detector roller that is pressed against a press-roller for detecting the relative movements of a pull cord or a Bowden cable used for mechanically rotating or sliding the ultrasonic transducer.

17. Method of claim 1 wherein said detector measures the position of the ultrasonic emitter and/or receiver mechanically.

18. Method of claim 17 wherein said detector measures the position of the ultrasonic emitter and/or receiver at least substantially continuously during emitting and receiving.

19. Method of claim 1 wherein said detector measures the position of the ultrasonic emitter and/or receiver optically.

20. Method of claim 1 further comprising, during emitting and/or receiving of ultrasonic waves:
detecting the various positions of said ultrasonic emitter and/or said ultrasonic receiver in increments; and
associating each of the detected positions with a corresponding image sub-area.

21. Method of claim 20 further comprising:
associating a corresponding time stamp with each of the image sub-areas.

22. Method of claim 20 wherein the number of incrementally detected positions is more than the number of image sub-areas.

23. Device for recording ultrasonic images of an object, comprising:
an ultrasonic emitter for emitting ultrasonic waves onto the object, and an ultrasonic receiver for receiving ultrasonic waves reflected by said object, wherein said ultrasonic emitter and/or said ultrasonic receiver is/are displaced and/or rotated, at least partly, relative to said object for recording individual image sub-areas, and wherein
said ultrasonic emitter and/or said ultrasonic receiver is/are provided for manual displacement along said object and/or for manual rotation, at least partly, relative to said object, and wherein
a separate detector incrementally detects the positions of said ultrasonic emitter and/or said ultrasonic receiver relative to said object and associates them with the individual image sub-areas, and
said detector is mounted on said ultrasonic emitter and/or ultrasonic receiver and measures the position of the ultrasonic emitter and/or receiver mechanically or optically.

24. Device according to claim 23, wherein
an incremental transmitter is provided for incremental detection of the movement, and said detector detects the positions of said ultrasonic emitter and/or said ultrasonic receiver relative to said object in a manner not synchronized with the recording of individual image sub-areas of said object.

25. Device according to claim 23, wherein
a plurality of incremental transmitters is provided for incremental detection of the movement with two to six degrees of freedom of an ultrasonic transducer.

26. Device according to claim 23, wherein
said detector is integrated into said ultrasonic emitter and/or said ultrasonic receiver or in said ultrasonic transducer, respectively.

27. Device according to claim 23, wherein
said increment detector detects the rotational movement of the ultrasonic transducer in steps by means of a wheel.

28. Device according to claim 23, wherein
said increment detector is a detector roller that is pressed against a press-roller for detecting the relative movements of a pull cord or a Bowden cable used for mechanically rotating or sliding the ultrasonic transducer.

* * * * *